United States Patent [19]

Fukuda

[11] 4,254,105

[45] Mar. 3, 1981

[54] MULTIPLE EMULSION HAVING A FORM OF WATER/OIL/WATER PHASE AND PROCESS FOR PREPARATION THEREOF, AND MULTIPLE EMULSION TYPE COSMETICS

[75] Inventor: Hidenori Fukuda, Odawara, Japan

[73] Assignee: The Lion Dentifrice Co., Ltd., Tokyo, Japan

[21] Appl. No.: 922,905

[22] Filed: Jul. 10, 1978

Related U.S. Application Data

[62] Division of Ser. No. 731,253, Oct. 12, 1976, abandoned.

[30] Foreign Application Priority Data

Oct. 11, 1975 [JP] Japan ................................. 50/122717
Sep. 6, 1976 [JP] Japan ................................. 51/106487

[51] Int. Cl.$^2$ ..................... A61K 31/00; A61K 31/46; A61K 31/70
[52] U.S. Cl. ................................... 424/170; 424/172; 424/180; 424/365
[58] Field of Search ................ 252/312; 424/170, 172, 424/365, 180

[56] References Cited

U.S. PATENT DOCUMENTS

| | | | |
|---|---|---|---|
| 2,114,490 | 4/1938 | Harris | 252/311 |
| 2,508,978 | 5/1950 | Tribble | 252/522 |

FOREIGN PATENT DOCUMENTS 1235667  6/1971  United Kingdom ..................... 424/168

*Primary Examiner*—Stanley J. Friedman
*Attorney, Agent, or Firm*—Jordan and Hamburg

[57] ABSTRACT

A multiple emulsion having a dispersing form of water-phase/oil-phase/water-phase and a process for preparation thereof, and a multiple emulsion type cosmetics utilizing said multiple emulsion as a fundamental form, said multiple emulsion consisting of a dispersed phase and a dispersion medium, of which the dispersed phase is a water-in-oil type emulsion formed by dispersing water phase into oil phase which consists of an oil component and a oil-soluble emulsifier having such a hydrophile-lipophile balance that the oil component forms a dispersion medium of the water-in-oil type emulsion, and of which the dispersion medium is an aqueous solution which contains an water-soluble emulsifier having such a hydrophile-lipophile balance that the oil component forms a dispersion medium of an oil-in-water type emulsion and having such concentration that the oil-soluble emulsifier does not dissolved therein.

5 Claims, 10 Drawing Figures

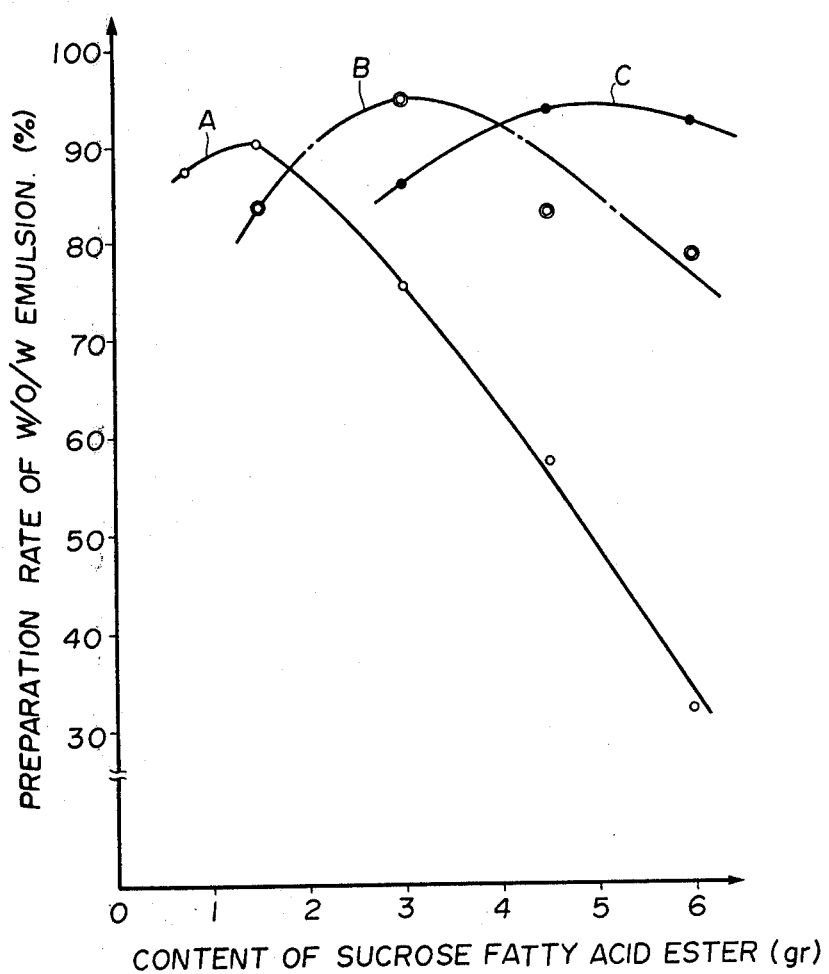

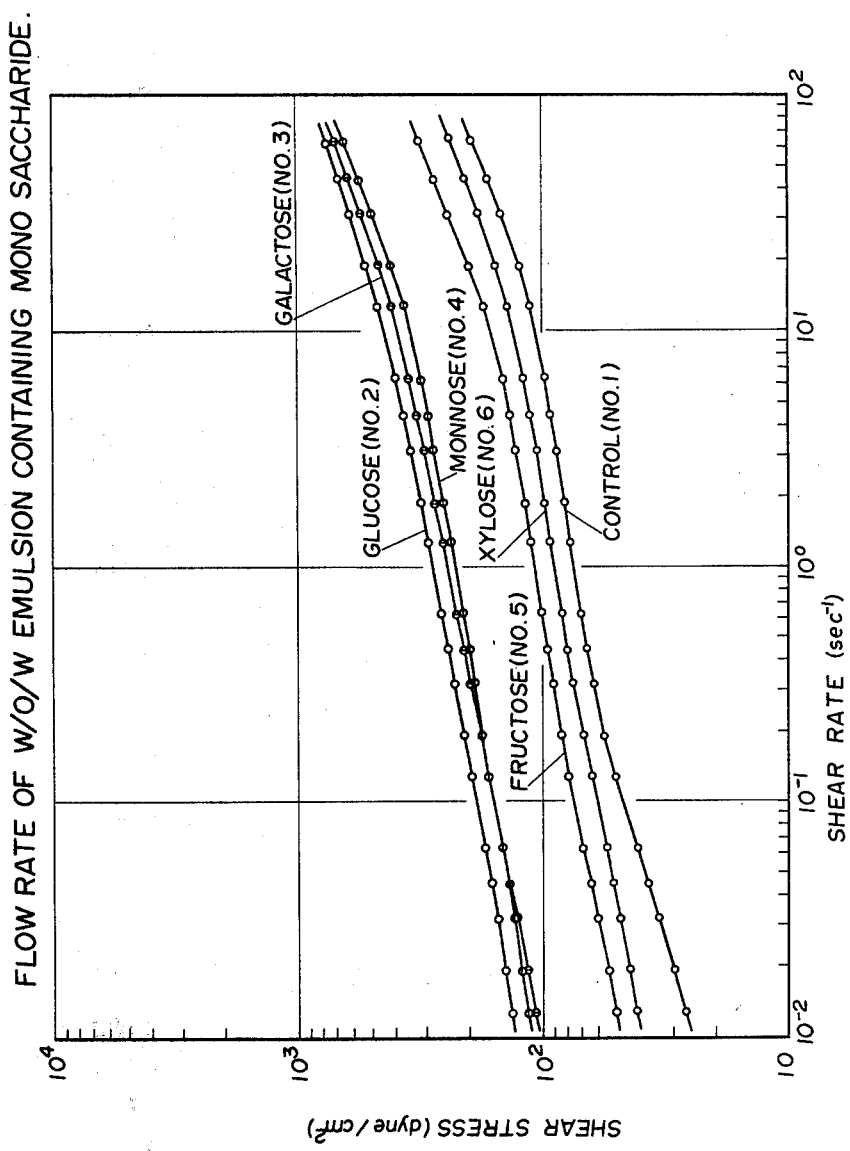

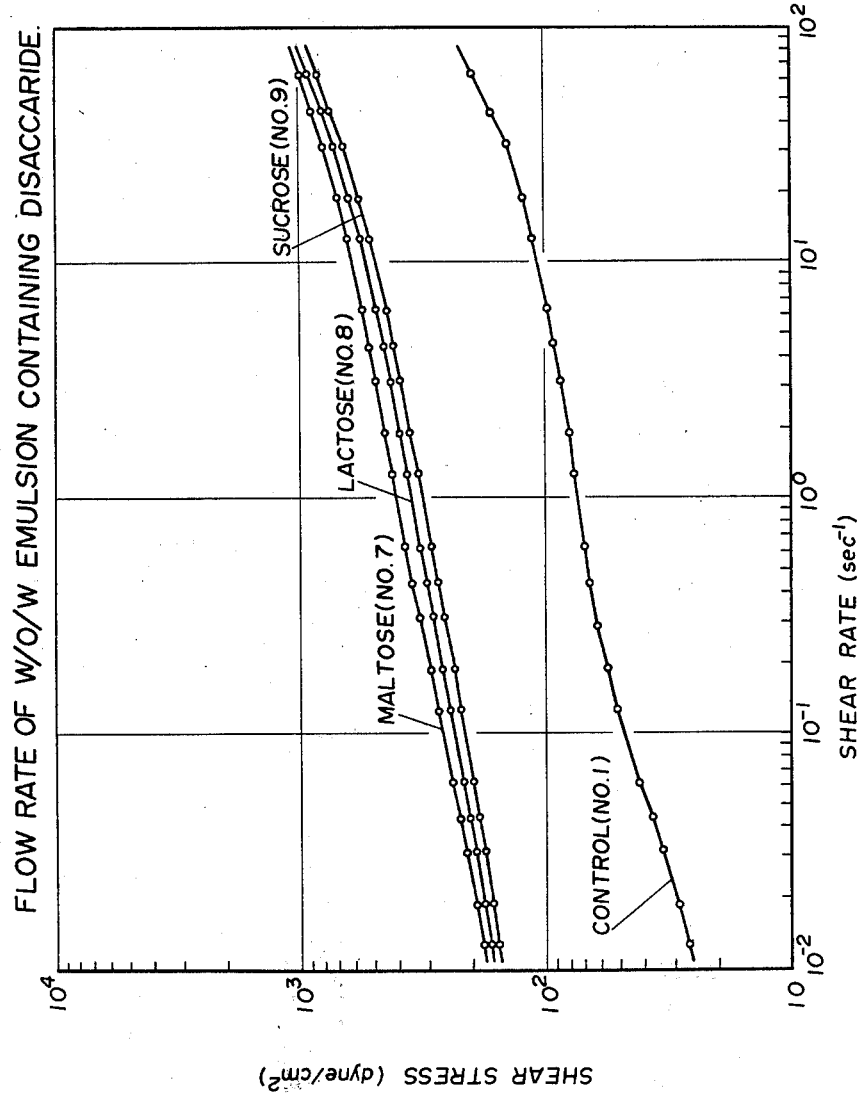

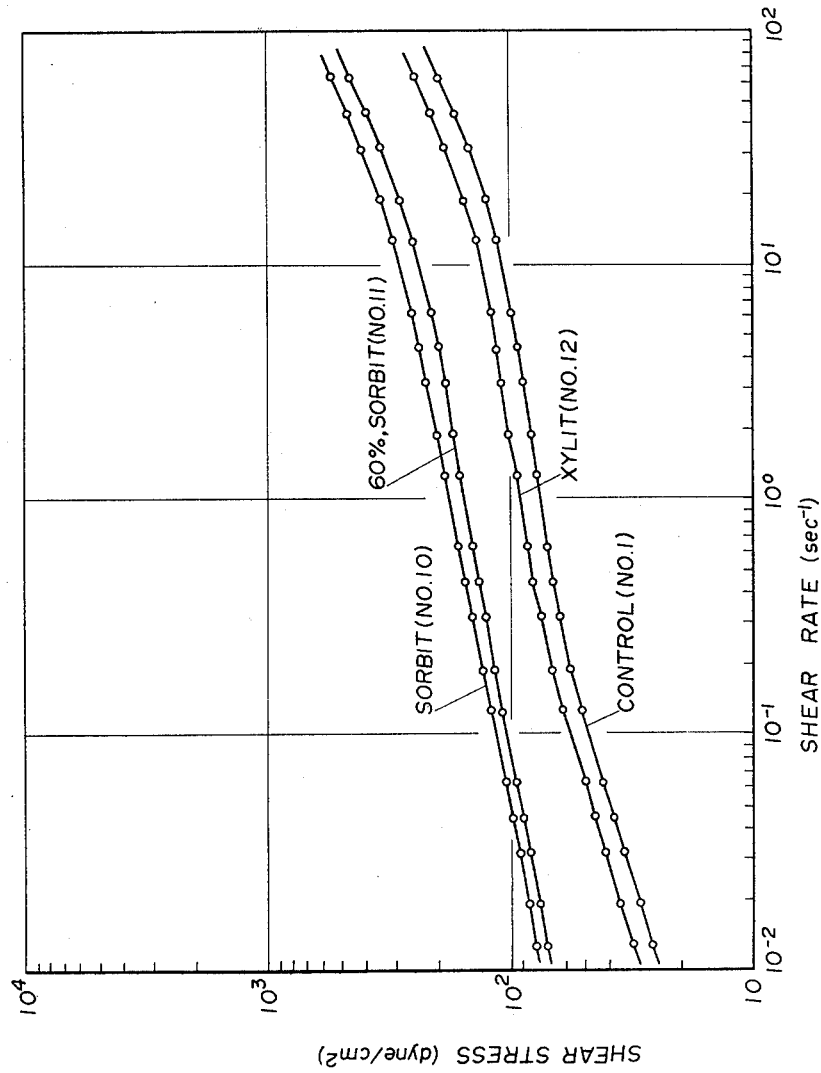

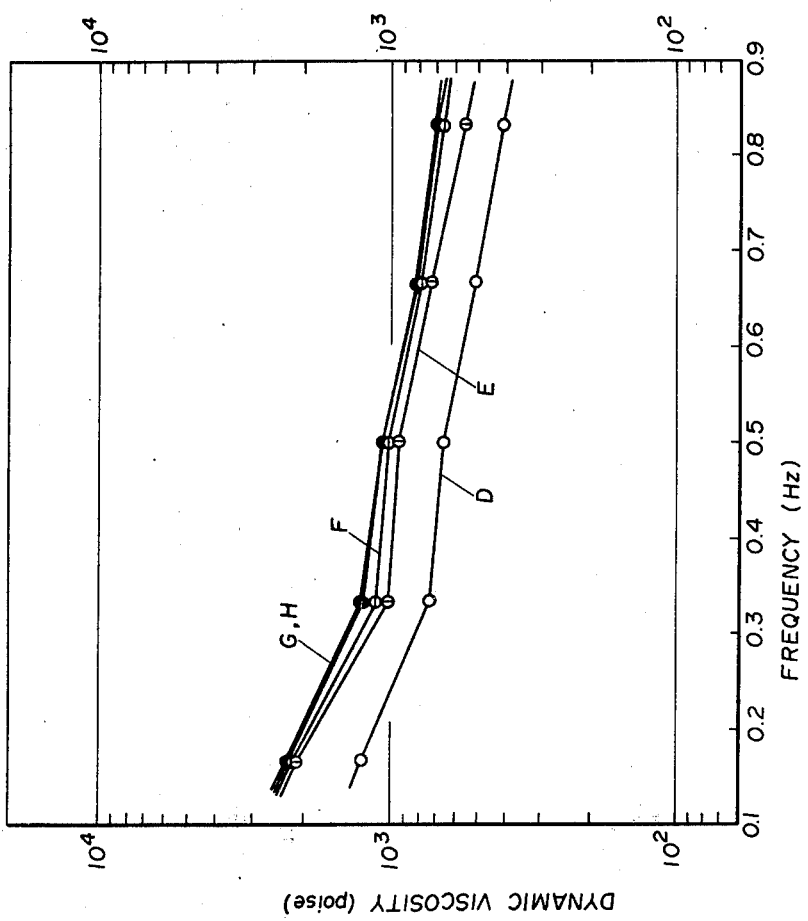

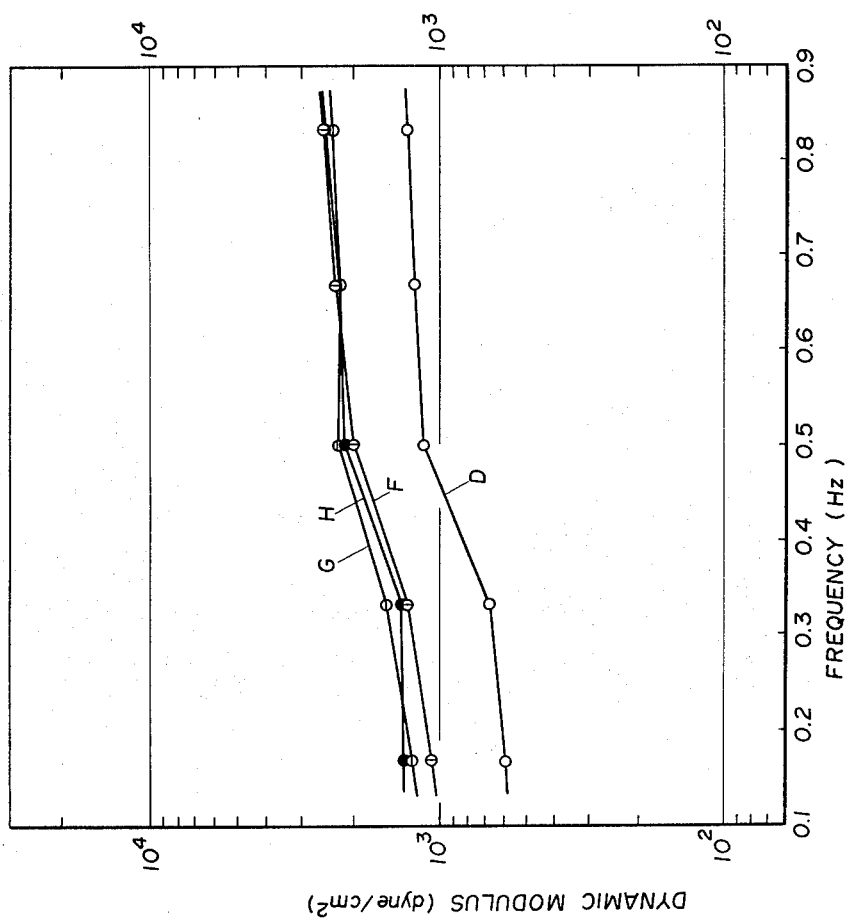

MULTIPLE EMULSION HAVING A FORM OF WATER/OIL/WATER PHASE AND PROCESS FOR PREPARATION THEREOF, AND MULTIPLE EMULSION TYPE COSMETICS

This is a division of application Ser. No. 731,253 filed Oct. 12, 1976, now abandoned.

BACKGROUND OF THE INVENTION

The present invention relates to a multiple emulsion having the form of water-phase/oil-phase/water-phase (hereinafter designated as "W/O/W multiple emulsion") which may be used as the fundamental form for various products requiring emulsified dispersion system such as cosmetics, drugs, foods and drinks, etc., and also relates to a process for preparing the multiple emulsion and a cosmetics having the form of the multiple emulsion.

Conventionally, the single emulsions such as oil-in-water type emulsion (hereinafter designated as "O/W emulsion") and water-in-oil type emulsion (hereinafter designated as "W/O emulsion") have been widely utilized as the fundamental form for various chemical products. For example, cosmetics such as creams and lotions mostly use W/O emulsion or O/W emulsion as their fundamental form.

Widely used W/O emulsion type cosmetic creams have the advantages of very smooth appearance, high cleansing effect and excellent emolient effect. They give, however, sticky or oily feelings because their external oil phase are exposed to skin on application. The emulsion stability is reduced if water content exceeds 50 vol % in W/O emulsion. On the other hand, O/W emulsion type cosmetic creams have disadvantages of less cleansing and emolient effects than W/O emulsion type creams although they have the many advantages of excellent extensibility and well refreshing feeling on their application. Since emulsion type lotions are made as a form of O/W emulsion in general, they have not only similar disadvantages as described above, but have often caused the problem of creaming showing unstability.

W/O/W multiple emulsion, which may eliminate both disadvantages of W/O and O/W emulsions, may be utilized as a fundamental form for various products such as cosmetics. The formation of the multiple emulsion, however, unexpectedly occurs during preparation of single type emulsion. There is little reproducibility in preparation of multiple emulsion in addition to extremely low proportion of the multiphase-emulsified particles (the low preparation rate of the multiple emulsion) and extremely poor stability of the multiple emulsion. After all, multiple emulsion is very difficult to be prepared and has not been sufficiently utilized.

SUMMARY OF THE INVENTION

The first object of the present invention is to provide a W/O/W multiple emulsion with high preparation rate and high stability.

Another object of the invention is to provide a W/O/W emulsion with high viscoelasticity in addition with high preparation rate and high stability.

A further object of the invention is to provide a process for preparing a W/O/W emulsion, by which the stable W/O/W emulsion with high preparation rate can be easily and consistently produced with high reproducibility.

Still a further object of the invention is to provide cosmetics consisting of a form of W/O/W emulsion which have both advantages of O/W and W/O emulsions, so that the cosmetics can have excellent cleansing and emolient effect, high extensibility and very confortable feelings on the application, and also eliminate the possibility of the occurrence of creaming.

The multiple emulsion having a form of water-phase/oil-phase/water-phase in accordance with the present invention consists of a dispersed phase and a dispersion medium, of which said dispersed phase is a water-in-oil type emulsion formed with water phase and oil phase which is obtained by dissolving an oil-soluble emulsifier having such a hydrophile-lipophile balance as that an oil component forms a dispersion medium of the water-in-oil type emulsion, into the oil component, and of which the dispersion medium is an aqueous solution containing a water-soluble emulsifier having such a hydrophile-lipophile balance that the oil component forms a dispersed phase of an oil-in-water type emulsion, to the extent that the oil-soluble emulsifier is not dissolved therein, and the resulting multiple emulsion has high preparation rate of the multiple particle therein and is extremely stable so that, for instance, even after 5-month storage at room temperature, no decomposition of this multiple emulsion can be observed, that is, there is no difference in the state of the multiple emulsion immediately after preparation and that after 5-month storage.

Furthermore, if at least one saccharide selected from the group consisting of monosaccharides, oligosaccharides and sugaralcohols is dissolved in the water phase of W/O emulsion that is the dispersed phase of the W/O/W emulsion the proportion of multiphase-emulsified particles in the resulting W/O/W emulsion considerably becomes higher due to addition of the saccharide such as glucose than a W/O/W emulsion without any saccharide added.

The addition of the saccharide enables the preparation rate of the multiple particles to be increased from twice to 4 times according to the result of their microscopic observation, and according to the viscosity measurement from 1.5 to 5.5 times.

The reason why saccharide addition improves the properties of the W/O/W emulsion may be explained by the fact that the formation of a complex between the saccharide and certain functional group, e.g., sorbitan portion, of the surface active agent through hydrogen bond increases mechanical strength of the inter-facial film of the W/O emulsion, allowing the W/O emulsion, that is dispersed phase of the W/O/W emulsion, to exist sufficiently stable in the dispersion medium.

In this case, monosaccharides or disaccharides may cause important influences due to their unique structure. Additionally, the higher the proportion of the multiphase-emulsified particles in the W/O/W emulsion, the higher is the viscosity of the multiple emulsion. The reason is that the true volume proportion of the dispersed phase increases as the proportion of multiphase-emulsified particles increases, and causes a proportional change in viscosity.

The process for preparing the multiple emulsion having a form of water/oil/water phase according to the present invention comprises dissolving an oil-soluble emulsifier having such a hydrophile-lipophile balance that an oil component forms a dispersion medium of a W/O emulsion, into the oil component; adding water to the resulting solution to form a W/O emulsion; and finally adding this W/O emulsion to an aqueous solution which is prepared by dissolving a water-soluble emulsifier having such a hydrophile-lipophile balance that the oil component forms a dispersed phase of an O/W emulsion, into water, to the extent that the oil-soluble emulsifier used for the formation of the W/O emulsion does not dissolve therein; and emulsifying the W/O emulsion as a dispersed phase into the aqueous solution. This process allows stable W/O/W emulsions having various dispersed phase volume to be easily and consistently prepared with high reproducibility and high preparation rate of the multiple particles.

The W/O/W emulsion is effective as a fundamental form for chemical products such as foods, drinks and drugs, etc., and it is particularly effective as a fundamental form for cosmetics such as creams and lotions. Therefore, the cosmetics according to the present invention is made by utilizing the W/O/W emulsion described above as its fundamental form, and has both advantages of W/O and O/W emulsions. The cosmetic creams such as cleansing creams and nourishing creams made by the utilization of the W/O/W emulsion as a fundamental form have very smooth and excellent appearance, good extensibility permitting them to be easily and uniformly extended to a thin film on skin. The creams have no sticky and oily feeling but refreshed feeling at the initial stage on their application, and also have very comfortable feeling similar to W/O type creams after their extension on skin. They offer excellent cleansing and emolient effects, thus allowing the effects of their pharmacentical components to be fully manifested. In addition, since the dispersed phase (internal phase) of the W/O/W emulsion is the W/O emulsion, much water may be contained in the internal phase as compared to the internal phase consisting of only oil component such as seen in O/W emulsion. This means that difference in density between the internal phase and the continuous phase (the external aqueous phase) can be reduced to an extremely small degree. Therefore, it is not necessary to use a stabilizer to reduce creaming rate. Accordingly, the viscosity of the continuous phase and dispersed phase volume can be easily controlled and thus emulsion type lotions with a wide range of viscosity can be produced. Other and further objects, features and advantages of the present invention will appear more fully from the following descriptions.

BRIEF DESCRIPTION OF THE DRAWINGS

FIG. 3 is a graph showing the preparation rate of the W/O/W emulsion in relation to the content of the oil-soluble emulsifier and that of the water-soluble emulsifier.

FIGS. 6-8 are graphs showing the relation between shear stress and shear rate as to the W/O/W emulsion to which one of monosaccharides, disaccharides and sugaralcohols is added, respectively.

FIG. 9 is a graph showing the effect of glucose on dynamic viscosity of a W/O emulsion.

FIG. 10 is a graph showing the effect of glucose on dynamic modulus of a W/O emulsion.

DETAILED DESCRIPTION

Figure 1:
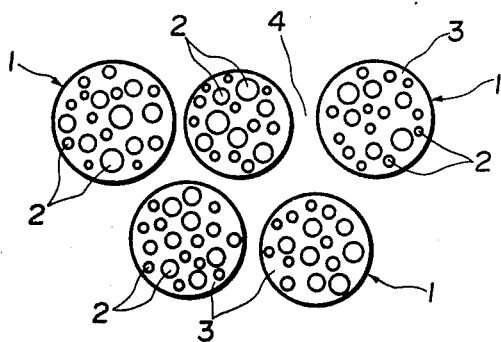
FIG. 1 shows an outline of the state of the W/O/W multiple emulsion according to the present invention.

As a oil component, which is used for the formation of W/O emulsion, almost all animal fats and oils, vegetable fats and oils, mineral oils and waxes are used. One or more of the appropriate fats, oils and waxes may be selectively used for various purposes. For the preparation of cosmetics one or more of oil components which are conventionally used, such as animal fats and oils, vegetable fats and oils, hardened oils, waxes as carnauba wax and beeswax, higher hydrocarbons as liquid paraffin and paraffin wax, and fatty acids as stearic acid, may be appropriately selected and used for their purposes. The amount of these oil components to be added may be determined depending on, e.g., the type of product to be manufactured, but its maximum amount will be determined by the maximum volume percentage of the W/O emulsion in the W/O/W emulsion and also by the minimum volume percentage of the water phase in that W/O emulsion, and in order to fully utilize the advantages of the W/O/W emulsion, the maximum amount of the oil component should be 52.5 vol. % in the W/O/W emulsion in this invention. On the other hand, the minimum amount is not specifically determined, but is preferably 7.5 vol. % for manufacturing products such as cosmetics.

The oil-soluble emulsifier to be used for the formation of the W/O emulsion from the oil components described above should have such an appropriate hydrophile—lipophile balance (hereinafter designated as "HLB") that the oil component used can form the dispersed phase of the W/O emulsion. Non-ionic active agent, particularly sorbitan fatty acid ester such as sorbitan mono-stearate and sorbitan mono-oleate, can be preferably used as the emulsifier and the mixture of the sorbitan mono-fatty acid esters may also be used. The amount of the oil-soluble emulsifier to be added varies depending on the types of the oil component and the oil-soluble emulsifier itself, and is usually 1–20% (wt/vol) of the amount of the oil component used, but it is favorably 3% (wt/vol) or higher because the addition of sorbitan fatty acid ester in the concentration above 3% (wt/vol) allows the W/O emulsion of which particles have average diameter $1\mu$ or smaller and are dispersed uniformly when observed by an optical microscope until the volume percentage of its water phase reaches 70%, to be prepared.

The water phase to be dispersed in the oil component is distilled or deionized water or an aqueous solution consisting of the water and certain water-soluble components required for the preparation of the products such as cosmetics, for examples, ascorbic acid and urea. The amount of the distilled or deionized water or the aqueous solution to be added may be properly determined depending on the type of products to be manufactured, but is in general in the range of 30–75 vol. % of the W/O emulsion. Then, it is preferable to make the water phase volume above 30% (vol/vol) in order to fully utilize the advantages of the W/O/W emulsion, whereas the properties of the resulting W/O/W emulsion become similar to those of the O/W emulsion if the water phase volume is less than 30% (vol/vol). On the other hand, if the water phase volume in the W/O emulsion exceeds 75% (vol/vol), stability of the W/O emulsion itself decreases and it may cause the preparation rate of the multiple particles to be reduced.

Additionally, at least one saccharide selected from the group consisting of monosaccharides, oligosaccharides and sugaralcohols may be dissolved into the water or the aqueous solution, and the use of the solution containing the saccharide enables the viscosity of the W/O/W emulsion to be increased and the preparation rate of the multiphase-emulsified particles to be further raised. For example, glucose, galactose, mannose, fructose and xylose as monosaccharide, maltose, lactose and sucrose as oligosaccharide, sorbit and xylit as sugaralcohol, and the mixture thereof may be used. In such a case, the effect to increase both the proportion of multiphase-emulsified particles and the viscosity of the W/O/W emulsion is greater in addition of oligosaccharides, particularly in disaccharides, and nextly greater in addition of monosaccharides than in that of sugaralcohols, and hence, in order to obtain the multiple emulsion with higher proportion of the multiphase-emulsified particles and greater viscosity, it is preferable to use maltose, lactose, sucrose, glucose and galactose. The amount of the saccharide to be added is preferably ranged between 0.1 and 20% (wt/vol) in the water phase (i.e. the internal phase of the W/O emulsion). The reason of this is that if the concentration of the saccharide is less than 0.1%, insufficient inter-action between the saccharide and the specified functional group such as sorbitan part of the oil-soluble emulsifier may result, while if it exceeds 20%, the resulting W/O emulsion becomes less stable because of physical effects such as osmotic pressure. Thus, the most preferable amount of such saccharides to be added is 5% (wt/vol) in the water phase. Further, apart from the components described above, those as perfumes and coloring agents, may also be added, and in such a case, it is preferable to have previously dissolved the oil-soluble components in the oil component and the water-soluble components in the water phase, respectively.

The water-soluble emulsifier to be used in this invention is an emulsifier having a HLB at which the aforementioned oil component can form the dispersed phase of the O/W emulsion. As the water-soluble emulsifier, surface active agents which have various ranges of HLB may be used since the stability of the W/O emulsion, that is the dispersed phase in the W/O/W emulsion, is very excellent because of the addition of the saccharides; for examples, as *non-ionic surface active agents,* sucrose fatty acid ester, polyoxyethylene sorbitan fatty acid ester such as polyoxyethylene sorbitan mono-oleate, polyoxyethylene sorbitan mono-laurate, polyoxyethylene sorbitan mono-palmitate, polyoxyethylene sorbitan mono-stearate, polyoxyethylene sorbitan tri-stearate and polyoxyethylene sorbitan tri-oleate; polyoxyethylene sorbitol fatty acid ester such as polyoxyethylene solbitol mono-laurate; polyoxyethylene fatty acid ester such as polyoxyethylene stearate, polyoxyethylene oleate and polyoxyethylene laurate; polyoxyethylene higher alcoholic ether such as polyoxyethylene cetyl alcohol and polyoxyethylene lauryl alcohol; polyoxyethylene alkyl aryl ether such as polyoxyethylene octyl phenol and polyoxyethylene nonyl phenol; polyoxypropylene polyoxyethylene higher alcohol such as polyoxypropylene polyoxyethylene cetyl alcohol; and alkylol amide such as lauryl ethanol amide may be used; as *anionic surface active agents* fatty acid soap such as sodium laurate; salt of higher alcoholic sulfuric acid ester such as lauryl sodium sulfate; salt of secondary higher alcoholic sulfuric acid ester; salt of higher fatty acid ester sulfuric acid ester; salt of higher fatty acid alkylol amide sulfuric acid ester; and alkyl aryl sulfonate such as alkyl benzene sulfonate; as *cationic surface active agents,* salt of primary amine; quaternary ammonium salt; and pyridonium alkyl halide; as *amphoteric surface active agents,* N-lauryl amino-propionate; and as *natural surface active agents,* lecithin may be used; while it is most preferable to use sucrose fatty acid ester and polyoxyethylene sorbitan fatty acid ester and the mixture thereof. The water-soluble emulsifier is dissolved in water to form an aqueous solution of the emulsifier, and in this solution antioxidant and antiseptic agent may also be added if necessary. The amount of the emulsifier to be added varies depending on the type of the emulsifier used and other conditions, but its preferable range is 0.3–30% (wt/vol) of the amount of the oil component described above, in general. However, the amount of the water-soluble emulsifier to be added must be within such a range that the oil-soluble emulsifier used for the formation of the W/O emulsion does not dissolve therein. Thus in case where sucrose fatty acid ester is used as the watersoluble emulsifier, the amount of the sorbitan fatty acid ester (the oil-soluble emulsifier) is, in general, 0.5–3.0 parts in weight, preferably 0.7–2.7 parts per 1 part in weight of sucrose fatty acid ester, while in case of polyoxyethylene sorbitan fatty acid ester used, sorbitan fatty acid ester is 1–15 parts in weight, preferably 5–12 parts per 1 part in weight of polyoxyethylene sorbitan fatty acid ester.

Accordingly, in preparing the W/O/W emulsion which consists of the W/O emulsion as a dispersed phase and the aqueous solution of the watersoluble emulsifier as a dispersion medium, the volume percentage of the W/O emulsion may reach up to 75 vol. %, thus the volume percentage of the aqueous solution of the water-soluble emulsifier may be reduced to 25 vol. %, and the W/O/W emulsion is extremely stable even when such a great amount of W/O emulsion is dispersed in the aqueous solution of the water-soluble emulsifier. On the other hand, the minimum volume percentage of the W/O emulsion in the W/O/W emulsion may be infinitely small theoretically, while in utilizing it as a fundamental form of an emulsion type cosmetics, the minimum amount of the W/O emulsion is preferably 25 vol. %, that is, the maximum amount of the aqueous solution of water-soluble emulsifier is preferably 75 vol. %, in order to permit the product to have fully the functions as cosmetics. Therefore, the amount of the water-soluble emulsifier to be added is selected properly within the range described above.

The followings describe the method for producing W/O/W multiple emulsion by using the components described above.

For this purpose, first, W/O emulsion is prepared from the oil component and the water or the aqueous solution which may contain at least one saccharide selected from the group consisting of monosaccharides, oligosaccharides, sugaralcohols and/or other components. In this preparation of the W/O emulsion, the oil-soluble emulsifier is added to and dissolved in the oil component to make oil phase, and a predetermined amount of the aqueous phase is added to the oil phase. The mixture is agitated for a specified period of time and so the oil phase forms continuous phase (i.e., dispersion medium), in which the aqueous phase is dispersed, resulting in the formation of the W/O emulsion. In this procedure, during the dissolution of the oil-soluble emulsifier in the oil component and during agitation of the mixture of the oil phase and the aqueous phase, it is preferable to heat these systems on the occasion of using certain kind of the oil-soluble emulsifier. For example, in case of sorbitan monostearate, these systems may be heated to about 70° C. It is also preferable to agitate the systems by a homomixer at a fixed rate of rotation for a specified period of time.

Then, this W/O emulsion is added to an aqueous solution prepared by dissolving water-soluble emulsifier in water to form a W/O/W multiple emulsion. In this process, it is also preferable to heat the aqueous solution of the water-soluble emulsifier and the W/O emulsion on the occasion of using certain kind of the water-soluble emulsifier. For example, in case of sucrose fatty acid ester, the aqueous solution of the water-soluble emulsifier heated to 70° C. is gently agitated using a homomixer with the W/O emulsion preheated to 70° C. and the final mixture is more agitated and emulsified for the specified period of time so that the multi-phase particles once formed are not broken. The W/O/W multiple emulsion prepared according to this process is shown in FIG. 1, in which the W/O/W emulsion consist of W/O emulsion 1 as a dispersed phase (i.e., internal phase) having internal water phase 2 dispersed in oil phase 3, and external water phase 4 as a dispersion medium (i.e., continuous phase).

The optimal period of time required for agitation in preparing the W/O/W emulsion by adding W/O emulsion to aqueous solution of the water-soluble emulsifier, varies depending on the emulsification equipment used, but it is not preferable to agitate for hours since the preparation rate of the W/O/W emulsion may be rapidly reduced because of physical conditions such as efficiency of agitation, and thus it is recommendable to predetermine the agitation time for the emulsification equipment so that the preparation rate of the W/O/W emulsion will be as high as possible. It is also preferable to consider that, in general, the longer the agitation time the smaller is the average diameter of the particles of the dispersed phase in the W/O/W emulsion in predetermining the agitation time. The cosmetics according to the present invention utilizes such a W/O/W multiple emulsion as its fundamental form. Various cosmetics such as emolient cream, cleansing cream, foundation cream, massage cream, nutrient cream, hand cream, hair cream and other creams, and emolient lotion, cleansing lotion, after-shaving lotion, suntan lotion, hand lotion, hair-treatment lotion and other lotions, are manufactured with W/O/W multiple emulsion form. The followings give preferred embodiments which show the characteristics of the present invention in detail. Various modifications and changes in their details are comprehended within the scope of the appended claims.

First, some of the examples are described for purpose of explanation of the invention in more detail.

EXAMPLE 1

Each of 6 g, 10 g and 14 g of the mixture (Span type emulsifier) of sorbitan mono-stearate (1 part) and sorbitan mono-oleate (1 part) was separately added to 100 ml of soft liquid paraffin to prepare three kinds of solutions. To each of the solutions 220 ml of water was added at 70° C. with stirring and then the mixture were further agitated and emulsified to prepare corresponding three kinds of W/O emulsions. By adding each of 0.75 g, 1.5 g, 3.0 g, 4.5 g and 6.0 g of sucrose fatty acid ester to 100 ml of water and then dissolving, five kinds of aqueous solutions were prepared. Subsequently, to each of the aqueous solutions each of the W/O emulsions preheated to 70° C. was separately added at 70° C. with stirring so that the volume percentage of the W/O emulsion became 50%, and each resulting mixture was agitated with a homomixer and emulsified to prepare 15 kinds of W/O/W emulsion. The preparation rate of each W/O/W emulsion was shown in Table 1, and all of these W/O/W emulsion were very stable.

TABLE 1

| Amount of Span type emulsifier | The preparation rate of the W/O/W emulsion | | | | |
|---|---|---|---|---|---|
| | Amount of sucrose fatty acid ester | | | | |
| | 0.75 g | 1.5 g | 3.0 g | 4.5 g | 6.0 g |
| A 14 g (4.7 g) | W/O | W/O | 85.9% | 93.5% | 92.5% |
| B 10 g (3.3 g) | 90.6% | 83.8% | 95.0% | 82.9% | 78.4% |
| C 6 g (1.2 g) | 87.6% | 90.2% | 75.5% | 57.2% | 32.0% |

In the above table, the figures in parentheses show the amount of the Span type emulsifier in W/O/W emulsion, "W/O" represents that W/O emulsion was formed but W/O/W emulsion was not formed. By plotting the data in Table 1 a graph shown in FIG. 3 was obtained. Further, the result of Table 1 is summarized in FIG. 2 with respect to relation between amount of the Span type emulsifier and that of sucrose fatty acid ester.

Figure 2:
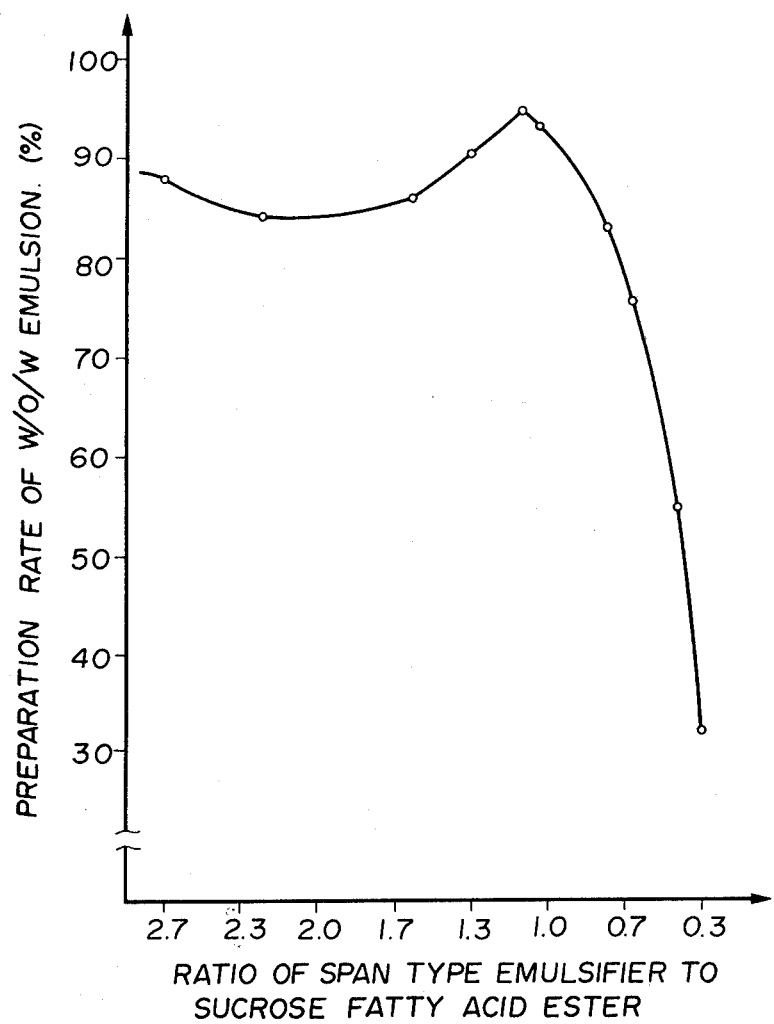
FIG. 2 is a graph showing the preparation rate of the W/O/W emulsion (the proportion of the multiphase-emulsified particles) according to the present invention, in relation to the content ratio between the oil-soluble emulsifier and the water-soluble emulsifier.

As shown in FIG. 2, if the ratio of the Span type emulsifier to sucrose fatty acid ester is approximately 1.1, the preparation rate of W/O/W emulsion is maximum, while if it is above 1.5, the rate is kept at almost constantly high level, and further if it is below 0.7, the rate rapidly lowers. The reason why the preparation rate of multiple emulsion lowers as the ratio lowers may be explained by that the increase in the proportion of sucrose fatty acid ester in relation to the Span type emulsifier allows the latter to be made soluble in the former and therefore the W/O/W emulsion to be easily broken. On the other hand, the reason why the preparation ratio of multiple emulsion becomes maximum at the ratio of 1.1 may be explained by that easiness of competitive adsorption of the sucrose fatty acid ester and the Span type emulsifier on the interface of multiple emulsion allows mechanical strength of the interfacial film to be increased, and thus the multiple emulsion once formed to be broken with much difficulty. In the meantime, if the ratio exceeds 2.7, W/O/W emulsion is often inverted to W/O emulsion. From this point of view, it may be said that the maximum ratio of the Span type emulsifier to sucrose fatty acid ester is about 3.0.

With respect to the fact described above, therefore, for increasing the preparation rate of W/O/W emulsion, it is preferable to increase the amount of Span type emulsifier if the amount of sucrose fatty acid ester to be added has been increased.

EXAMPLE 2

5 g of sorbitan mono-stearate and 5 g of sorbitan mono-oleate were added to 100 ml of soft liquid paraffin and dissolved therein at 70° C., and then 220 ml of water was added to the solution at 70° C. with stirring. The resulting mixture was further agitated to prepare W/O emulsion. 3 wt/vol. % of sucrose fatty acid ester was added to water to prepare aqueous solution. To the aqueous solution, the W/O emulsion preheated to 70° C. was added at 70° C. under agitation so that the volume percentage of the W/O emulsion became 35%, 50% and 62.5% respectively. Subsequently, each of the mixture was agitated by a homomixer for 10 minutes to obtain three kinds of W/O/W emulsions with the preparation rate 73%, 95% and 93%, respectively. Stability of all these emulsions was very high. The graph of the preparation rate of W/O/W emulsion in relation to the amount of W/O emulsion (i.e., dispersed phase volume) is illustrated in FIG. 4.

Figure 4:
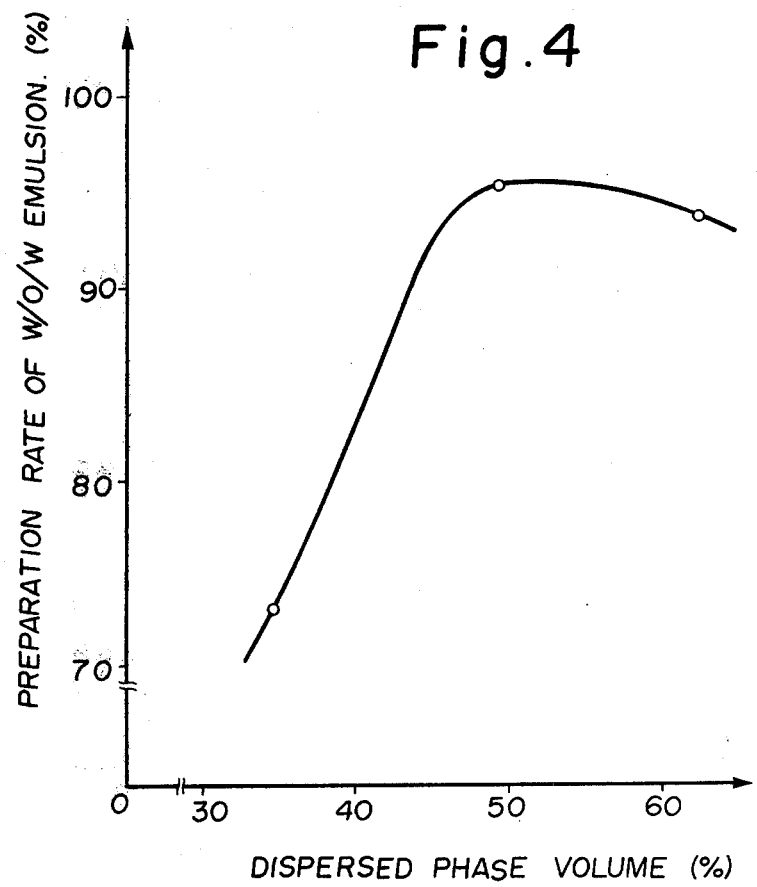
FIG. 4 is a graph showing the preparation rate of the W/O/W emulsion in relation to its dispersed phase volume.

As seen in FIG. 4, in preparing the W/O/W emulsion, the preparation rate of the emulsion becomes almost constant after the dispersed phase volume exceed a certain level, while if the dispersed phase is low, the preparation rate decreases. For example, as seen in FIG. 4, where the dispersed phase volume ranges between 50% and 75%, the preparation rate is kept at almost constant level, while if the dispersed phase volume is less than 35%, the preparation rate decreases considerably. It is, therefore, preferable to predetermine agitation time and other parameters at optimal conditions so as to obtain the maximum preparation rate of the multiple emulsion at any specified volume percentage of dispersed phase.

EXAMPLE 3

Figure 5:
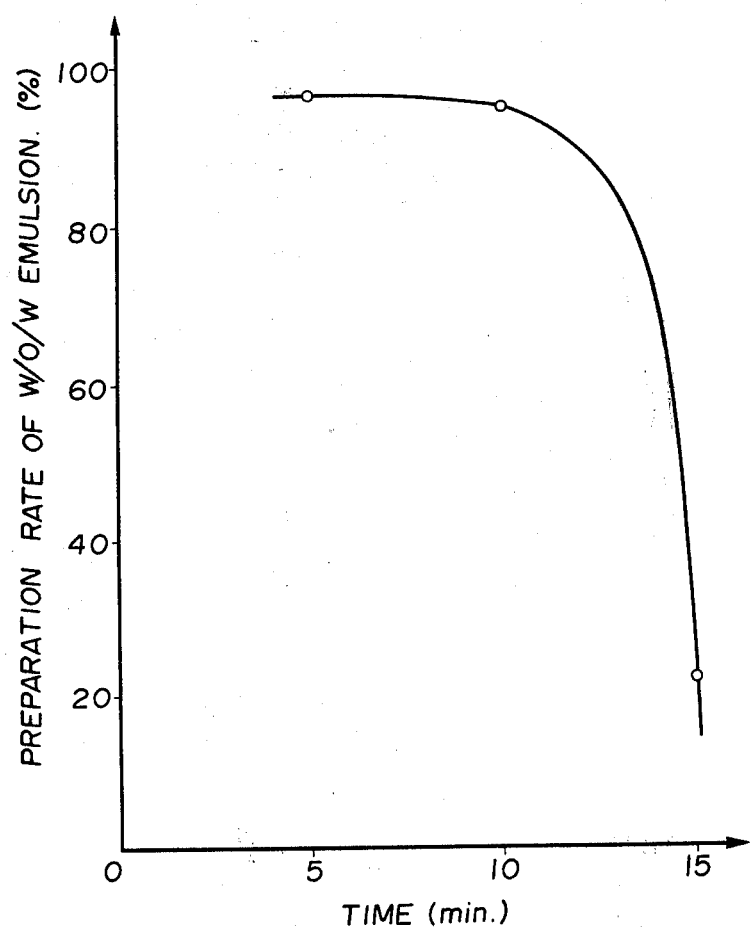
FIG. 5 is a graph showing the preparation rate of the W/O/W emulsion in relation to the agitation time.

5 g of sorbitan mono stearate and 5 g of sorbitan mono-oleate were added to 100 ml of soft liquid paraffin and dissolved at 70° C. therein. Next, 220 ml of water was added to the solution at 70° C. under agitation, followed by further agitation to form W/O emulsion consisting of the paraffin as a continuous phase. 3 g of sucrose fatty acid ester was dissolved in 100 ml of water to form aqueous solution. To the aqueous solution gently agitated at 70° C., approximately 100 g of the W/O emulsion preheated to 70° C. was added under agitation by a homomixer for 5 minutes until a W/O/W emulsion was formed. The preparation rate of the W/O/W emulsion was about 96% and the product was very stable. Another W/O/W emulsion was also prepared in the same method except the agitation time by a homomixer of 10 minutes, with its preparation rate of about 95%. The latter emulsion was also very stable. In the meanwhile, the preparation rate of the multiple emulsion prepared with agitation time by a homomixer of 15 minutes was so much decreased to as about 22%. FIG. 5 shows the relation between the preparation rate of W/O/W emulsion and agitation time.

In FIG. 5, agitation time by a homomixer within 10 minutes allows the preparation rate of the multiple emulsion to be kept at high level almost constantly, while such an agitation time of 15 minutes remarkably reduces the rate. It follows, therefore, that too long period of time of agitation is not preferable.

EXAMPLE 4

Similarly to Example 3, W/O emulsion and an aqueous solution of water soluble emulsifier were prepared. Subsequently, the W/O emulsion preheated to 70° C. was added to the aqueous solution at 70° C. under agitation so that the volume percentage of the W/O emulsion became 50%, and then the mixture was agitated by a homomixer for 5 minutes to form W/O/W emulsion. This W/O/W emulsion was stored at room temperature for five months after preparation. The emulsion was observed with an optical microscope at 600 magnifications just after preparation, two days, a week, two weeks, a month and five months after preparation. According to the microscopic photographs thus obtained, the W/O/W emulsion formed as above is extremely stable, and there is almost no change in the state of the emulsion even after five-month storage at room temperature and in addition, almost no decomposition of dispersing particles in the emulsion.

EXAMPLE 5

A mixture of 1 part of sorbitan mono-stearate and 1 part of sorbitan mono-oleate was dissolved in liquid paraffin, and then an aqueous solution in which one or more of saccharides had been previously dissolved was added at 70° C. under agitation thereto, followed by further agitation for emulsification, with consequent W/O emulsion of which dispersed phase was the aqueous solution containing one or more of saccharides. An aqueous solution of water-soluble emulsifier was prepared by dissolving a mixture of sucrose fatty acid esters of HLB 11 and HLB 14 into water. Subsequently, each of the W/O emulsions preheated to 70° C. was added to the aqueous solution at 70° C. under agitation, followed by further agitation for emulsification, with consequent W/O/W emulsion of those compositions as summarized in Table 2. For comparison, W/O/W emulsion, of which composition shows also in Table 2, was prepared similarly but without blending any saccharide into the innermost aqueous phase. FIGS. 6–8 are also the relation between shear rate and shear stress for these emulsion. (These curves were plotted based upon measurement by means of thixotrometer manufactured by Iwamoto Maufacturer, Co. Ltd., Japan at 23° C.)

Further, Table 3 shows the apparent viscosity of each W/O/W emulsion at shear rate of $1.0 \text{ sec}^{-1}$, calculated from FIGS. 6–8.

It can be seen from microscopic photographs that the proportion of the multiphase-emulsified particles in the multiple emulsion containing the saccharide is higher than that in the multiple emulsion containing no saccharide (Sample No. 1). According to FIGS. 6–8, as saccharide was added, the flow curves of the emulsions containing saccharide shifted upward along the axis of shear stress in parallel to and above that of the emulsion containing no saccharide. Further, with respect to relation between the viscosity and photographs by optical microscope for respective W/O/W emulsions, it is apparent that the higher the proportion of such multiphase-emulsified particles the higher is the viscosity.

TABLE 2

| | Composition of the W/O/W emulsions containing saccharides (wt/wt %) | | | | | | | | | Sugaralcohols | | |
|---|---|---|---|---|---|---|---|---|---|---|---|---|
| | | Monosaccharides | | | | | Disaccharides | | | | 60% | |
| Saccharides Sample No. | Control (1) | Glucose (2) | Galactose (3) | Monnose (4) | Fructose (5) | Xylose (6) | Maltose (7) | Lactose (8) | Sucrose (9) | Sorbit (10) | sorbit (11) | Xylit (12) |
| Internal water | 42.93 | 42.42 | 42.43 | 42.42 | 42.42 | 42.42 | 42.79 | 42.53 | 42.44 | 42.49 | 42.52 | 42.64 |

TABLE 2-continued

| | | Composition of the W/O/W emulsions containing saccharides (wt/wt %) | | | | | | | | | | |
|---|---|---|---|---|---|---|---|---|---|---|---|---|
| | | | Monosaccharides | | | | | Disaccharides | | | Sugaralcohols | | |
| Saccharides Sample No. | | Control (1) | Glucose (2) | Galactose (3) | Monnose (4) | Fructose (5) | Xylose (6) | Maltose (7) | Lactose (8) | Sucrose (9) | Sorbit (10) | 60% sorbit (11) | Xylit (12) |
| Component | phase Saccharide | 0 | 0.285 | 0.285 | 0.285 | 0.285 | 0.285 | 0.287 | 0.285 | 0.285 | 0.285 | 0.171 | 0.286 |
| | Sorbitan mono-stearate | 1.43 | 1.42 | 1.42 | 1.42 | 1.42 | 1.42 | 1.44 | 1.43 | 1.42 | 1.43 | 1.43 | 1.43 |
| | Sorbitan mono-oleate | 1.43 | 1.42 | 1.42 | 1.42 | 1.42 | 1.42 | 1.44 | 1.43 | 1.42 | 1.43 | 1.43 | 1.43 |
| | Liquid paraffin | 24.47 | 24.34 | 24.35 | 24.34 | 24.34 | 24.34 | 24.55 | 24.41 | 24.35 | 24.38 | 24.34 | 24.47 |
| | External water phase | 27.22 | 27.55 | 27.53 | 27.55 | 27.55 | 27.45 | 26.98 | 27.37 | 27.53 | 27.42 | 27.57 | 27.22 |
| | Sucrose fatty acid ester | | | | | | | | | | | | |
| | HLB 11 | 1.68 | 1.71 | 1.71 | 1.71 | 1.71 | 1.71 | 1.67 | 1.69 | 1.70 | 1.70 | 1.71 | 1.68 |
| | HLB 14 | 0.84 | 0.85 | 0.85 | 0.85 | 0.85 | 0.85 | 0.84 | 0.85 | 0.85 | 0.85 | 0.85 | 0.84 |

(Note 1)
*The internal water phase was calculated assuming that the preparation rate, viz., proportion of multiphase-emulsified particles formed was 100%.

TABLE 3

Apparent viscosity of the W/O/W emulsions containing various saccharides

| Sample No. | Saccharide | Apparent viscosity in poise, 1.0 sec$^{-1}$, 30° C. |
|---|---|---|
| 1 | (None) | 74.5 |
| 2 | Glucose | 280.0 |
| 3 | Galactose | 242.0 |
| 4 | Mannose | 228.0 |
| 5 | Fructose | 108.0 |
| 6 | Xylose | 90.0 |
| 7 | Maltose | 405.0 |
| 8 | Lactose | 350.0 |
| 9 | Sucrose | 320.0 |
| 10 | Sorbit | 179.0 |
| 11 | 60% sorbit | 155.0 |
| 12 | Xylit | 92.0 |

In addition, the result indicates that there is some difference in effect to increase viscosity of W/O/W emulsion, that is, effect to increase proportion of multiphase-emulsified particles between types of saccharides, and thus such the effect is particularly greater in disaccharides and monosaccharides.

In this connection, since all these W/O/W emulsions have almost same composition except the type of saccharides, it may be said that difference in properties between these W/O/W emulsions is to be attributed to presence of saccharide and types of saccharides. In addition, because of very low concentration of saccharide in W/O/W emulsion, this factor is not what changes physico-chemical properties of the whole system.

As has been described, addition of saccharide allows viscosity of W/O/W emulsion as well as proportion of the multiphase-emulsified particles to be increased, and this is due to the increase in mechanical strength of interfacial films of the W/O emulsion, that is dispersed phase of the W/O/W emulsion, and also the increase in stability of the W/O emulsion. This fact is illustrated in FIGS. 9–10; FIG. 9 shows the result of measurement on dynamic viscosity of the W/O emulsion in relation to amount of glucose added into the water phase of the W/O emulsion which was formed by adding 4.08 wt % of a mixture of sorbitan mono-stearate (1 part) and sorbitan mono-oleate (1 part) to liquid paraffin as oil phase so that dispersed phase (water phase) volume became 60%. FIG. 10 shows the results of effect of addition of glucose on dynamic modulus of the W/O emulsion prepared in a similar way. In FIGS. 9–10, D, E, F, G and H are characteristics corresponding to amount of glucose added, i.e., 0, 0.204, 0.407, 0.611 and 0.815 wt. %, respectively. Apparently from these results, addition of glucose enables dynamic viscosity and dynamic modulus of the W/O emulsion to be increased, and thus addition of saccharide such as glucose enables mechanical strength of interfacial film to be increased, and that allows viscosity of the W/O/W emulsion and the proportion of the multiphase-emulsified particles to be increased.

EXAMPLE 6

Each of the following three phases (1), (2) and (3) was prepared:

Phase (1): Oil phase made by dissolving 10.0 g of sorbitan mono-stearate and 10.0 g of sorbitan mono-oleate in 100 g of liquid paraffin and 70 g of white vaseline at 70° C.

Phase (2): Internal water phase made by dissolving 3.0 g of maltose in 200 ml of distilled water.

Phase (3): External water phase made by dissolving 9.0 g of sucrose fatty acid ester (of which HLB had been adjusted to be 12) in 100 ml of distilled water.

Then, (2) was added to (1) at 70° C., and the mixture was subjected to agitation by a homomixer for emulsification to prepare W/O emulsion.

200 g of the W/O emulsion was added to (3) preheated to 70° C., and the mixture was gently agitated by a homomixer to form W/O/W emulsion.

The W/O/W emulsion prepared as above was creamy and of high viscosity, and as compared to such a system with no maltose contained, its proportion of multiphase-emulsified particles was extremely higher.

Further, the product showed excellent feature of stability in storage, that is, even after 3-month storage at 40° C., decompositive phenomena in the dispersing system such as separation of liquid phases and creaming could not be observed at all.

EXAMPLE 7

Similarly, each of the following three phases (1), (2) and (3) was prepared:

Phase (1): Oil phase made by mixing 85 g of liquid paraffin and 85 g of olive oil, heating the mixture to 70° C. and dissolving 10 g of sorbitan mono-palmitate and 10 g of sorbitan mono-stearate therein.

Phase (2): Internal water phase made by dissolving 5.0 g of glucose in 300 ml of distilled water.

Phase (3): External water phase made by dissolving 6 g of sucrose fatty acid ester featuring HLB 11, and 3.0 g of polyoxyethylene sorbitan mono-stearate in 100 ml of distilled water.

Subsequently, (2) was added to (1) at 70° C., and the mixture was subjected to agitation by a homomixer for emulsification to prepare W/O emulsion.

250 g of the W/O emulsion was added to (3) preheated to 70° C., and the mixture was gently agitated by a homomixer, with consequent W/O/W emulsion.

Similarly, the W/O/W emulsion prepared as above was creamy and of high viscosity, and as compared to such a system with no glucose contained, its proportion of the multiphase-emulsified particles was extremely higher.

EXAMPLE 8

Similarly, each of the following three phases (1), (2) and (3) was prepared:

Phase (1): Oil phase made by mixing 70 g of liquid paraffin, 50 g of olive oil and 50 g of refined lanolin and dissolving 15 g of sorbitan mono-stearate and 15 g of sorbitan mono-oleate therein.

Phase (2): Internal water phase made by dissolving 6.0 g of sorbitol in 200 ml of distilled water.

Phase (3): External water phase made by dissolving 6.0 g of polyoxyethylene sorbitan tri-stearate and 3.0 g of polyoxyethylene sorbitan mono-stearate in 100 ml of distilled water.

Subsequently, (2) was added to (1) at 70° C., and the mixture was subjected to agitation by a homomixer for emulsification to prepare W/O emulsion.

200 g of the W/O emulsion was added to (3) preheated to 70° C., and the mixture was gently agitated by a homomixer, to form W/O/W emulsion.

The W/O/W emulsion prepared as above was creamy but slightly fluid, and as compared to such a system with no sorbitol contained, its proportion of the multiphase-emulsified particles was extremely high.

EXAMPLE 9

Similarly, each of the following three phases (1), (2) and (3) was prepared:

Phase (1): Oil phase made by mixing 50 g of liquid paraffin, 30 g of white vaseline, 50 g of refined lanolin and 40 g of olive oil and dissolving 15.0 g of sorbitan mono-stearate at 70° C. therein.

Phase (2): Internal water phase made by dissolving 4.0 g of lactose in 250 ml of distilled water.

Phase (3): External water phase made by dissolving both 4.0 g of sucrose fatty acid ester featuring HLB 14 and 8.0 g of sucrose fatty acid ester featuring HLB 11 in 100 ml of distilled water.

Subsequently, (2) was added to (1) at 70° C., and the mixture was subjected to agitation by a homomixer for emulsification to prepare W/O emulsion.

200 grams of the W/O emulsion was added to (3) preheated to 70° C., and the mixture was gently agitated by a homomixer, to form W/O/W multiple emulsion.

The W/O/W multiple emulsion prepared as above was creamy and of high elasticity as if it were slightly gelled, and as compared to such a system with no lactose contained, its proportion of the multiphase-emulsified particles was extremely high.

Stability of these W/O/W emulsion prepared according to the procedures seen in Examples 7–9 was similar to that of Example 6.

Some of the experimental embodiments are described with respect to characteristics of cosmetics utilizing such a W/O/W multiple emulsion as its fundamental form in the following:

EXAMPLE 10: NUTRIENT CREAM

First, W/O emulsion having the following composition was prepared:

| Beeswax | 10.0 wt. % |
| --- | --- |
| Ceresine | 10.0 |
| Vaseline | 15.0 |
| Lanolin | 5.0 |
| Cosbiol | 15.0 |
| Olive oil | 12.0 |
| Sorbitan mono-oleate | 4.0 |
| Sorbitan mono-stearate | 3.0 |
| Sucrose | 1.5 |
| Distilled water | 23.5 |
| Perfume | 1.0 |
| Total | 100.0 wt. % |

The W/O emulsion having the above mentioned composition was much more stable than an emulsion with no sucrose. Subsequently, the W/O emulsion having the above mentioned composition was dispersed in an aqueous solution of sucrose fatty acid ester, and the mixture was emulsified at 70° C. by a homomixer, with consequent W/O/W nutrient cream having the following composition.

| Composition of W/O/W Nutrient Cream: | |
| --- | --- |
| W/O emulsion of the above mentioned composition | 78 wt. % |
| Sucrose fatty acid ester (HLB = 12) | 2.0 |
| Distilled water | 20.0 |
| Antioxidant and antiseptic | Proper qt. |

The obtained nutrient cream featured very refreshing feeling on application, and so high extensibility that very thin film consisting of its oil component could be easily formed. Thus the nutrient cream proved to be excellent.

In comparison with such a system with no sucrose, the proportion of multiphase-emulsified particles and viscosity in steady flow were much higher. Further, it had so high storage stability that neither creaming nor separation could be observed even after storage at 40° C. for three months.

EXAMPLE 11: SUNTAN LOTION

First, W/O emulsion having the following composition was prepared:

| Liquid paraffin | 28.5 wt. % |
| --- | --- |
| Olive oil | 15.0 |
| Sunscreen agent | 3.0 |
| Sorbitan mono-oleate | 3.0 |

| | |
|---|---|
| Glucose | 1.5 |
| Distilled water | 49.0 |
| Perfume | Proper qt. |

The W/O emulsion having the above mentioned composition was extremely stable in emulsified state in spite of its having high content of dispersed phase because of addition of glucose in the water phase.

Subsequently, the W/O emulsion having the above mentioned composition was dispersed in an aqueous solution of polyoxyethylene sorbitan monostearate, and the mixture was emulsified by a homomixer at room temperature to form W/O/W suntan lotion having the following composition.

| Composition of W/O/W Suntan Lotion: | |
|---|---|
| W/O emulsion of the above mentioned composition | 40.0 wt. % |
| Polyoxyethylene sorbitan mono-stearate | 0.2 |
| Distilled water | 59.8 |
| Antioxidant and antiseptic | Proper qt. |

The obtained suntan lotion featured very high extensibility so that oil component and sunscreen agent, which refer to effective component for formation of uniform and natural suntan colour skin, could be extremely and uniformly extended over a wide area on skin, giving no sticky touch but very comfortable and refreshing feeling on application.

In addition, because glucose was added to the water phase of the W/O emulsion that is a dispersed phase of the W/O/W suntan lotion, the proportion of the multi-phase emulsified particles prepared was extremely high, and no creaming could be observed during one month of practical use in spite of no stabilizer.

What is claimed is:

1. Multiple emulsion type cosmetics having a dispersing form of water-phase/oil-phase/water-phase which consists of a dispersed phase and dispersion medium, of which said dispersed phase is a water-in-oil type emulsion formed with water phase in which maltose is dissolved and oil phase which is obtained by dissolving an oil-soluble emulsifier having such a hydrophile-lipophile balance that an oil component forms a dispersion medium of said water-in-oil type emulsion, into said oil component, and of which said dispersion medium is an aqueous solution containing a water-soluble emulsifier having such a hydrophile-lipophile balance that said oil component forms a dispersed phase of an oil-in-water type emulsion, to the extent that said oil-soluble emulsifier is not dissolved therein.

2. Multiple emulsion type cosmetics as claimed in claim 1, wherein concentration of said maltose is 0.1 to 20% by weight/volume in said water phase in which said maltose is dissolved.

3. Multiple emulsion type cosmetics as claimed in claim 2, wherein concentration of said oil component is 5.25 to 56.25% by volume of said multiple emulsion, and concentration of said oil-soluble emulsifier is 1 to 20% by weight of said oil component, and concentration of said water-soluble emulsifier is 0.3 to 30% by weight of said oil component.

4. Multiple emulsion type cosmetics as claimed in claim 3, wherein sorbitan fatty acid ester is used as said oil-soluble emulsifier and sucrose fatty acid ester is used as said water-soluble emulsifier, and the ratio of said sorbitan fatty acid ester to said sucrose fatty acid ester is 0.5 to 3.

5. Multiple emulsion type cosmetics as claimed in claim 3, wherein sorbitan fatty acid ester is used as said oil-soluble emulsifier and polyoxyethylene fatty acid ester is used as said water-soluble emulsifier, and the ratio of said sorbitan fatty acid ester to said polyoxyethylene fatty acid ester is 1 to 15.

* * * * *